(12) United States Patent
Li et al.

(10) Patent No.: US 11,147,988 B2
(45) Date of Patent: Oct. 19, 2021

(54) DOSAGE VERIFICATION METHOD FOR RADIOTHERAPY DEVICE, AND RADIOTHERAPY DEVICE

(71) Applicants: Shenzhen OUR New Medical Technologies Development Co., Ltd., Guangdong (CN); OUR UNITED CORPORATION, Shaanxi (CN)

(72) Inventors: Jinsheng Li, Xi'an (CN); Haifeng Liu, Xi'an (CN); Hao Yan, Xi'an (CN)

(73) Assignees: SHENZHEN OUR NEW MEDICAL TECHNOLOGIES DEVELOPMENT CO., LTD.; OUR UNITED CORPORATION

( * ) Notice: Subject to any disclaimer, the term of this patent is extended or adjusted under 35 U.S.C. 154(b) by 208 days.

(21) Appl. No.: 16/316,064

(22) PCT Filed: Jul. 8, 2016

(86) PCT No.: PCT/CN2016/089382
§ 371 (c)(1),
(2) Date: Jan. 8, 2019

(87) PCT Pub. No.: WO2018/006404
PCT Pub. Date: Jan. 11, 2018

(65) Prior Publication Data
US 2019/0262631 A1 Aug. 29, 2019

(51) Int. Cl.
*A61N 5/00* (2006.01)
*A61N 5/10* (2006.01)

(52) U.S. Cl.
CPC .............. *A61N 5/1071* (2013.01); *A61N 5/00* (2013.01); *A61N 5/1038* (2013.01)

(58) Field of Classification Search
CPC ...... A61N 5/1071; A61N 5/00; A61N 5/1038; A61N 5/103; A61N 5/1064
(Continued)

(56) References Cited

U.S. PATENT DOCUMENTS

| 2012/0076271 A1 | 3/2012 | Yan ................................ 378/65 |
| 2013/0214766 A1 | 8/2013 | Furlong et al. .......... 324/207.21 |
| 2015/0224342 A1 | 8/2015 | Baltes |

FOREIGN PATENT DOCUMENTS

| CN | 1438602 A | 8/2003 |
| CN | 103083820 A | 5/2013 |

(Continued)

OTHER PUBLICATIONS

Chinese Office Action, dated May 22, 2020, issued in corresponding Chinese Patent Application No. 201680087446.X. English translation. Total 17 pages.

(Continued)

*Primary Examiner* — John P Lacyk
(74) *Attorney, Agent, or Firm* — Ostrolenk Faber LLP

(57) ABSTRACT

A dosage verification method for a radiotherapy device includes: acquiring reference optical field information about radioactive rays, wherein the reference optical field information includes the dosage distribution of a reference optical field; acquiring actual optical field information about the radioactive rays; comparing and analyzing the acquired actual optical field information about the radioactive rays and the acquired reference optical field information; and determining whether the actual optical field information is in a range of pre-set optical field information, wherein the pre-set optical field information is optical field information determined according to the reference optical field information.

8 Claims, 4 Drawing Sheets

(58) Field of Classification Search
USPC .............................................................. 600/1
See application file for complete search history.

(56) References Cited

FOREIGN PATENT DOCUMENTS

| CN | 104548372 A | 4/2015 |
| CN | 104825178 A | 8/2015 |
| CN | 104933652 A | 9/2015 |
| CN | 105031833 A | 11/2015 |
| CN | 105447330 A | 3/2016 |

OTHER PUBLICATIONS

International Search Report dated Feb. 16, 2017 in corresponding PCT International Application No. PCT/CN2016/089382.
Written Opinion dated Feb. 16, 2017 in corresponding PCT International Application No. PCT/CN2016/089382.

DOSAGE VERIFICATION METHOD FOR RADIOTHERAPY DEVICE, AND RADIOTHERAPY DEVICE

CROSS-REFERENCE TO RELATED APPLICATION

This application is a national phase entry under 35 USC 371 of International Patent Application No. PCT/CN2016/089382 filed on Jul. 8, 2016, the entirety of which is incorporated herein by reference.

TECHNICAL FIELD

The present disclosure relates to the technical field of medical apparatus, and more particularly, to a dosage verification method for a radiotherapy device, and a radiotherapy device.

BACKGROUND

When radiotherapy is carried out using a radiotherapy device, radiation dosages shall be verified to ensure an output dosage to be consistent with an expected dosage in a treatment plan, so as to improve accuracy of the radiotherapy. In the existing dosage verification, a measurement is usually performed manually using a film or an ionization chamber, but manual measurement involves a complex process and entails a radiation risk. As a result, the efficiency and safety of the radiation dosage verification are low and the radiation dosage cannot be verified in real-time during a radiotherapy process.

SUMMARY

In view of this, the present disclosure provides a dosage verification method for a radiotherapy device, and a radiotherapy device, to solve the technical problem that the efficiency and safety of the existing radiation dosage verification are low and the radiation dosage cannot be verified in real-time during a radiotherapy process.

According to an embodiment of the present disclosure, a dosage verification method for a radiotherapy device is provided, which is applied to the radiotherapy device. The method includes: acquiring reference light field information about radioactive rays, wherein the reference light field information is initial light field information of the radiotherapy device and includes a dosage distribution of a reference light field; acquiring actual light field information about the radioactive rays, wherein the actual light field information is light field information generated according to received radioactive rays used for treatment during a radiotherapy process; comparing and analyzing the acquired actual light field information about the radioactive rays and the acquired reference light field information; and determining whether the actual light field information is in a range of pre-set light field information, wherein the pre-set light field information is light field information determined according to the reference light field information.

Optionally, the dosage verification method for the radiotherapy device further includes: storing the actual light field information, and determining a treatment plan according to the actual light field information; or adjusting the radiotherapy device such that the actual light field information is in the range of the pre-set light field information.

Optionally, storing the actual light field information and determining the treatment plan according to the actual light field information, specifically includes: storing the actual light field information, and adjusting a current treatment plan according to the actual light field information; or storing the actual light field information, and adjusting a next treatment plan according to the actual light field information.

Optionally, before adjusting the radiotherapy device, the dosage verification method for the radiotherapy device further includes: detecting attenuation data of a radioactive source and/or detecting accuracy error data of the radiotherapy device; and adjusting the radiotherapy device according to the detected attenuation data and/or the accuracy error data.

Optionally, during a radiotherapy process, the dosage verification method for the radiotherapy device further includes: determining whether the actual light field information exceeds a warning value; and sending a warning signal when the actual light field information exceeds the warning value.

Optionally, during the radiotherapy process, the dosage verification method for the radiotherapy device further includes: determining whether a time duration in which the actual light field information exceeds the warning value is within a pre-set time period, and stopping radiotherapy when the time duration exceeds the pre-set time period.

Optionally, the light field information further includes at least one of a light field shape, a light field position, a dosage of the radioactive rays, and an intensity distribution in a light field range.

According to another embodiment of the present disclosure, a radiotherapy device is further provided, which includes: a radioactive source for emitting radioactive rays; a detector for receiving the radioactive rays emitted by the radioactive source; and a processor for acquiring actual light field information about the radioactive rays according to the radioactive rays received by the detector, comparing and analyzing an acquired actual light field information of the radioactive rays and an acquired reference light field information, and determining whether the actual light field information is in a range of pre-set light field information, wherein the reference light field information is initial light field information of the radiotherapy device, the actual light field information is light field information generated according to the radioactive rays received by the detector during a radiotherapy process, and the pre-set light field information is light field information determined according to the reference light field information.

Optionally, the processor is further used for storing the actual light field information and determining a treatment plan according to the actual light field information, or used for adjusting the radiotherapy device according to the actual light field information, such that the actual light field information meets light field requirements in a radiotherapy planning system.

Optionally, the processor is further used for determining a time duration in which the actual light field information is within the range of pre-set light field information or in which the actual light field information exceeds the range of the pre-set light field information; for determining whether the time duration is within a pre-set time period, and for stopping radiotherapy when the time duration exceeds the pre-set time period.

Optionally, the processor being further used for storing the actual light field information and determining the treatment plan according to the actual light field information, specifically includes: the processor being used for storing the actual light field information, and adjusting a current treatment plan according to the actual light field information; or for storing the actual light field information, and adjusting a next treatment plan according to the actual light field information.

Optionally, the processor is further used for acquiring attenuation data of the radioactive source and/or detecting accuracy error data of the radiotherapy device; and for adjusting the radiotherapy device according to the attenuation data and/or accuracy error data detected.

Optionally, the processor is further used for determining whether the actual light field information exceeds a warning value; and for sending a warning signal or stopping radiotherapy when the actual light field information exceeds the warning value.

Optionally, the light field information further includes at least one of a light field shape, a light field position, a dosage of the radioactive rays, and an intensity distribution in a light field range.

Compared with the prior art, in the dosage verification method for a radiotherapy device and the radiotherapy device provided in the present disclosure, e whether the dosage distribution of the actual light field is within a range of dosage distribution of the pre-set light field information is determined by acquiring and analyzing the reference light field information and the actual light field information about the radioactive rays, so as to verify whether the radiation dosage of the current radiotherapy device conforms to the requirement of the expected dosage. This enables convenient, fast and accurate verification of the dosage of the radiotherapy device, and improves the efficiency and accuracy of radiation dosage verification. Furthermore, it does not need to measure the radiation dosage manually, and improves the safety of radiation dosage verification. Besides, dosage verification can be performed in real time during the radiotherapy process.

BRIEF DESCRIPTION OF THE DRAWINGS

In order to describe technical solutions in embodiments of the present disclosure more clearly, the accompanying drawings to be used in the description of embodiments will be introduced briefly. Obviously, the accompanying drawings to be described below are merely some embodiments of the present disclosure, and a person of ordinary skill in the art can obtain other drawings according to those drawings without paying any creative effort.

DETAILED DESCRIPTION

The technical solutions of the present disclosure are described in detail below with reference to the accompanying drawings and embodiments. Obviously, the described embodiments are merely some but not all of embodiments of the present disclosure. All other embodiments made on the basis of the embodiments of the present disclosure by a person of ordinary skill in the art without paying any creative effort shall be included in the protection scope of the present disclosure.

In the description of the present disclosure, it will be noted that the terms "first", "second" and the like are for illustration purposes only, and shall not be construed as indicating or implying relative importance. In the description of the present disclosure, it will be noted that the terms "connected" and "connection" shall be broadly understood unless expressly stated and limited otherwise. For example, fixed connection, detachable connection, and integral connection are all available; mechanical connection and electrical connection are both available; direct connection and indirect connection via intermediate media are both available. A person of ordinary skill in the art could understand the meanings of the above terms in the present disclosure according to specific scenarios. Besides, in the description of the present disclosure, unless otherwise stated, "plurality" means two or more.

Any process or method description in flow charts or described otherwise herein can be understood as a module, a fragment or a portion of a code of an executable instruction including one or more steps for implementing a specific logic function or process. Furthermore, scopes of preferred embodiments of the present disclosure include other implementations, in which the functions may be performed in a substantially simultaneous manner or in a reverse order, rather than in an order shown or discussed, according to the functions involved, which shall be understood by those skilled in the art of the embodiments of the present disclosure.

Figure 1:
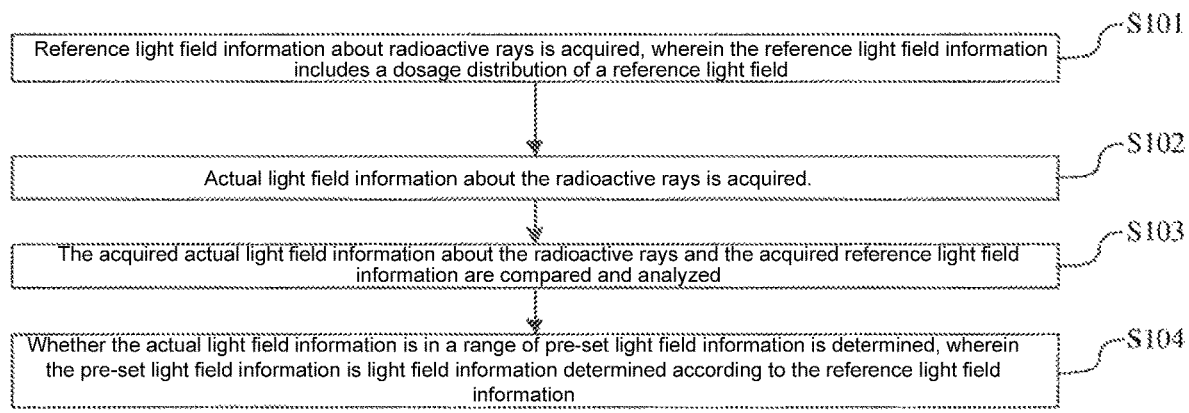
FIG. 1 is a schematic flow chart of a dosage verification method for a radiotherapy device according to an embodiment of the present disclosure.

FIG. 1 is a schematic flow chart of a dosage verification method for a radiotherapy device according to an embodiment of the present disclosure. As shown in FIG. 1, the dosage verification method for the radiotherapy device includes following steps.

In step S101, reference light field information about radioactive rays is acquired, wherein the reference light field information is initial light field information of the radiotherapy device and includes a dosage distribution of a reference light field.

The reference light field information refers to light field information configured in a radiotherapy plan when the radiotherapy device leaves the factory. The reference light field information may include such information as a dosage distribution of the reference light field, a shape of the light field, a location of the light field, a dosage of radioactive rays, and an intensity distribution of the radioactive rays in a range of the light field. In the present embodiment, when real-time dosage verification is performed, reference light field information about radioactive rays such as dosage distributions of the reference light field at various time points and treatment locations can be acquired from the radiotherapy planning system. In other embodiments, when non-real-time dosage verification is performed, pre-measured reference light field information about radioactive rays such as the dosage distribution of the reference light field can also be acquired by confirming an opening degree of a collimator with a size to be measured according to actual needs and treatment experience. Of course, manners in which the reference light field information about the radioactive rays are acquired are not limited in embodiments of the present disclosure. For example, the reference light field information about the radioactive rays can also be obtained by manual input.

In step S102, actual light field information about the radioactive rays is acquired, wherein the actual light field information is light field information generated according to received radioactive rays used for treatment during a radiotherapy process.

In the present embodiment, when real-time dosage verification is performed, the actual light field information about the radioactive rays, such as a dosage distribution of the actual light field, a shape of the light field, a location of the light field, a dosage of the radioactive rays, and an intensity distribution of the radioactive rays in a range of the light field can be acquired sequentially during the radiotherapy process. In other embodiments, when non-real-time dosage verification is performed, the actual light field information about the radioactive rays, such as the dosage distribution of the actual light field can be acquired by opening the collimator according to the correspondingly preset opening degree.

In step S103, the acquired actual light field information about the radioactive rays and the acquired reference light field information are compared and analyzed.

Figure 2:
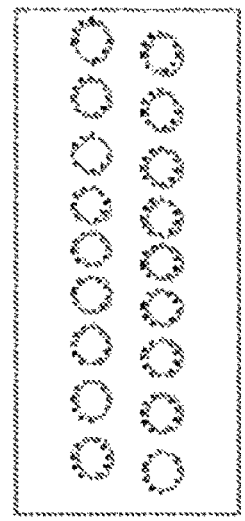
FIG. 2 is a schematic diagram of dosage distribution in a dosage verification method for a radiotherapy device according to an embodiment of the present disclosure.
Figure 3:
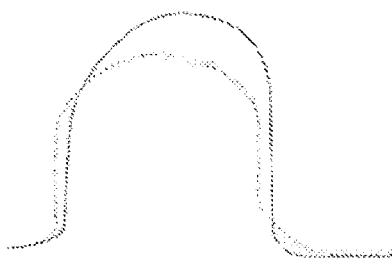
FIG. 3 is a schematic diagram of dosage distribution in a dosage verification method for a radiotherapy device according to another embodiment of the present disclosure.

In the present embodiment, the acquired actual light field information about the radioactive rays and the acquired reference light field information are compared and analyzed so that difference data between them is obtained through analysis, or relevance data between them are obtained through similarity index analysis. FIG. 2 is a schematic diagram of dosage distribution in a dosage verification method for a radiotherapy device in the present embodiment. As shown in FIG. 2, an example is taken in which a plurality of radiation sources emit radiation beams respectively, and each of the radiation beams forms a light field. The dotted portions in FIG. 2 are the reference light fields of the plurality of radiation sources acquired in the step S101, and the solid portions are the actual light fields of the plurality of radiation sources acquired in the step S102. As shown in FIG. 3, the dotted portion is a dosage distribution diagram of a reference light field of one of the radiation sources in the step S101, and the solid portion is a dosage distribution diagram of an actual light field thereof in the step S102. In embodiments of the present disclosure, the acquired dosage distribution of the actual light field of the radioactive rays and the acquired dosage distribution of the reference light field are compared and analyzed to confirm the difference between the dosage distribution of the actual light field and the dosage distribution of the reference light field, thereby giving a quantitative description of inconsistency between actual treatment beam data and theoretical beam data used in the planned treatment system. The inconsistency reflects a deviation of the dosage sent to a patient at the time of measurement. When the degree of inconsistency is within a tolerable range, the theoretical beam data can be updated to fine-tune the planning system, i.e. to adjust the treatment plan, so as to improve the consistency and correct the deviation of the transmitted dosage, thereby meeting the expected dosage requirements. When the degree of inconsistency exceeds a certain threshold, it indicates that the deviation of the transmitted dosage cannot be corrected through the planning system. At this time, the machine needs to be calibrated to make the actual beam meet the planning requirements again.

In step S104, whether the actual light field information is in a range of pre-set light field information is determined, wherein the pre-set light field information is light field information determined according to the reference light field information.

In the present embodiment, when the difference data or the relevance data after comparison and analysis does not exceed a preset threshold, it is determined that the actual light field information is in the range of the pre-set light field information, and it is verified that the radiation dosage of the current radiotherapy device meets the expected dosage requirements, then the radiation dosage may not be further adjusted. When the difference data or the relevance data after comparison and analysis exceeds the pre-set threshold, it is determined that the actual light field information is not in the range of the pre-set light field information, and it is verified that the radiation dosage of the current radiotherapy device does not meet the pre-set dosage requirements, then the radiation dosage may be further adjusted to meet the expected dosage requirements. Exemplarily, the adjustment of the radiation dosage may be completed by adjusting the device by an operator.

In the dosage verification method for a radiotherapy device in the present embodiment, whether the dosage distribution of the actual light field is in a range of dosage distribution of the pre-set light field is determined by acquiring and analyzing the reference light field information and the actual light field information of the radioactive rays, so as to verify whether the radiation dosage of the current radiotherapy device conforms to the requirement of the expected dosage. This enables convenient, fast and accurate verification of the dosage of the radiotherapy device, and improves the efficiency and accuracy of verification of the radiation dosage. Furthermore, it does not need to measure the radiation dosage manually, and improves the safety of radiation dosage verification. Besides, the dosage verification may be performed in real time during the radiotherapy process.

Figure 4:
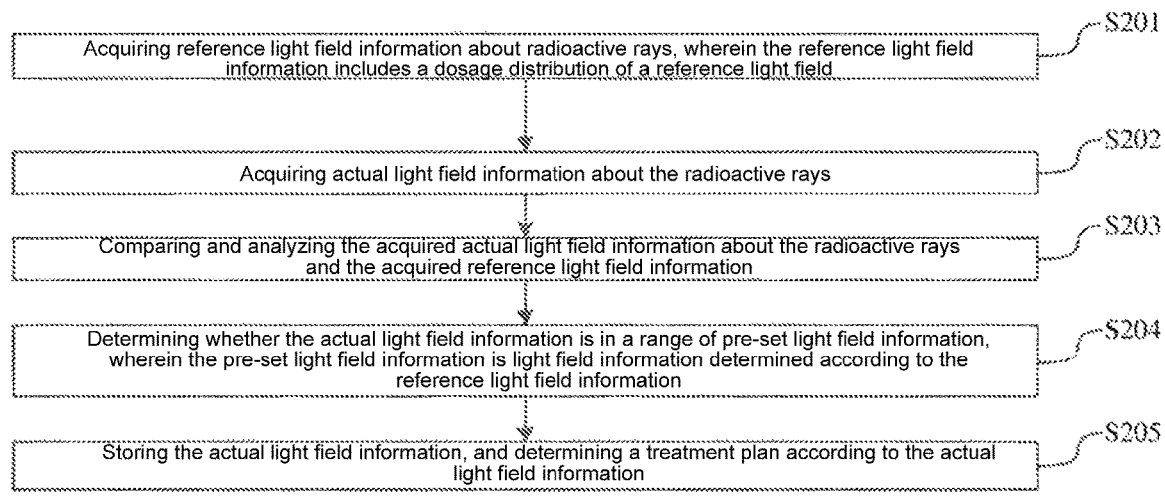
FIG. 4 is a schematic flow chart of a dosage verification method for a radiotherapy device according to yet another embodiment of the present disclosure.

FIG. 4 is a schematic flow chart of a dosage verification method for a radiotherapy device according to another embodiment of the present disclosure. As shown in FIG. 4, the dosage verification method for a radiotherapy device includes:

step S201: acquiring reference light field information about radioactive rays, wherein the reference light field information is initial light field information of the radiotherapy device and includes a dosage distribution of a reference light field;

Step S202: acquiring actual light field information about the radioactive rays, wherein the actual light field information is light field information generated according to received radioactive rays used for treatment during a radiotherapy process;

Step S203: comparing and analyzing the acquired actual light field information about the radioactive rays and the acquired reference light field information;

Step S204: determining whether the actual light field information is in a range of pre-set light field information, wherein the pre-set light field information is light field information determined according to the reference light field information.

Step S205: storing the actual light field information, and determining a treatment plan according to the actual light field information.

In the present embodiment, when the difference data or the relevance data after the comparison and analysis in the step S203 exceeds the pre-set threshold, it is determined in the step S204 that the actual light field information is not in the range of the pre-set light field information, and it is verified that the radiation dosage of the current radiotherapy device does not meet the pre-set dosage requirements. At this time, the radiation dosage needs to be further adjusted to meet the expected dosage requirements. Specifically, the actual light field information can be stored, and a current treatment plan or a next treatment plan can be adjusted according to the actual light field information. That is, the current treatment plan or the next treatment plan can be adjusted to compensate for the current radiotherapy, so that the radiation dosage received by the patient during the whole treatment process may meet the expected dosage requirements, so as to achieve precise treatment and improve the radiotherapy accuracy and therapeutic effect.

Exemplarily, the dosage of the radioactive rays in the actual light field information is smaller than that in the reference light field information, so adjusting the current treatment plan may be to extend the treatment duration, increase the intensity of the rays, etc., so as to make compensation in the current treatment. Alternatively, the treatment duration is extended or the intensity of the rays is increased in the next treatment plan to compensate for the intensity of the rays of this treatment in the next treatment.

Figure 5:
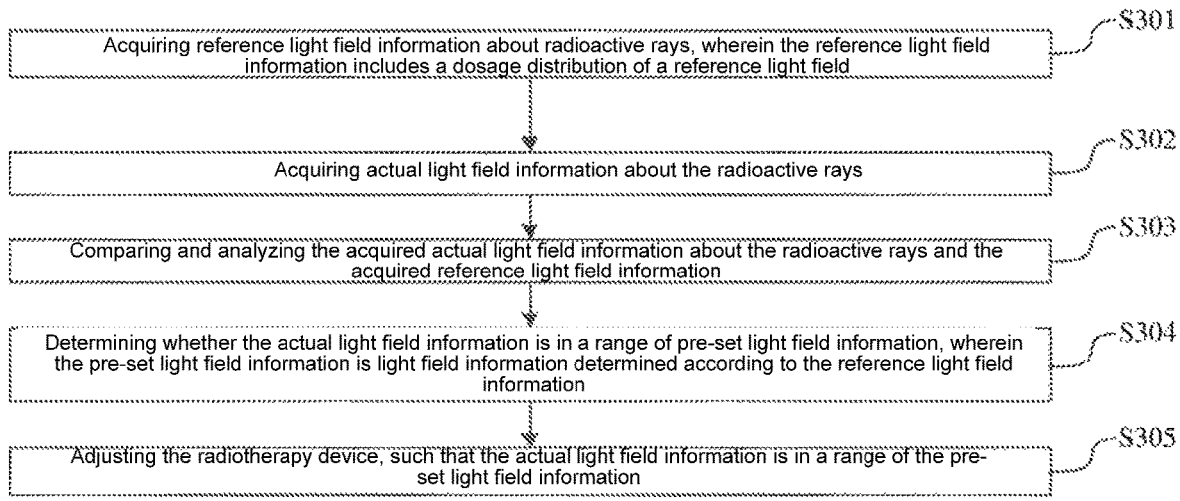
FIG. 5 is a schematic flow chart of a dosage verification method for a radiotherapy device according to yet still another embodiment of the present disclosure.

FIG. 5 is a schematic flow chart of a dosage verification method for a radiotherapy device according to yet still another embodiment of the present disclosure. As shown in FIG. 5, the dosage verification method for a radiotherapy device includes:

Step S301: acquiring reference light field information about radioactive rays, wherein the reference light field information is initial light field information of the radiotherapy device and includes a dosage distribution of a reference light field;

Step S302: acquiring actual light field information about the radioactive rays, wherein the actual light field information is light field information generated according to received radioactive rays used for treatment during a radiotherapy process;

Step S303: comparing and analyzing the acquired actual light field information about the radioactive rays and the acquired reference light field information;

Step S304: determining whether the actual light field information is in a range of pre-set light field information, wherein the pre-set light field information is light field information determined according to the reference light field information; and Step S305: adjusting the radiotherapy device, such that the actual light field information is in a range of the pre-set light field information.

In the present embodiment, when the difference data or the relevance data after the comparison and analysis in the step S303 exceeds the pre-set threshold, it is determined in the step S304 that the actual light field information is not in the range of the pre-set light field information, and it is verified that the radiation dosage of the current radiotherapy device does not meet the pre-set dosage requirements. At this time, the radiation dosage needs to be further adjusted to meet the expected dosage requirements. Specifically, in the present embodiment, a movement of a treatment couch or a treatment head can be controlled via a control system of the radiotherapy device to adjust a radial distance between the treatment head and a therapeutic target, so that the actual light field information falls within the range of the pre-set light field information, so as to adjust the radiation dosage to meet the expected dosage requirements, thereby achieving precise treatment and improving the radiotherapy accuracy and therapeutic effect. In other embodiments, hardware devices such as the treatment head or radioactive sources can be adjusted manually, such that the actual light field information falls within the range of the pre-set light field information.

Figure 6:
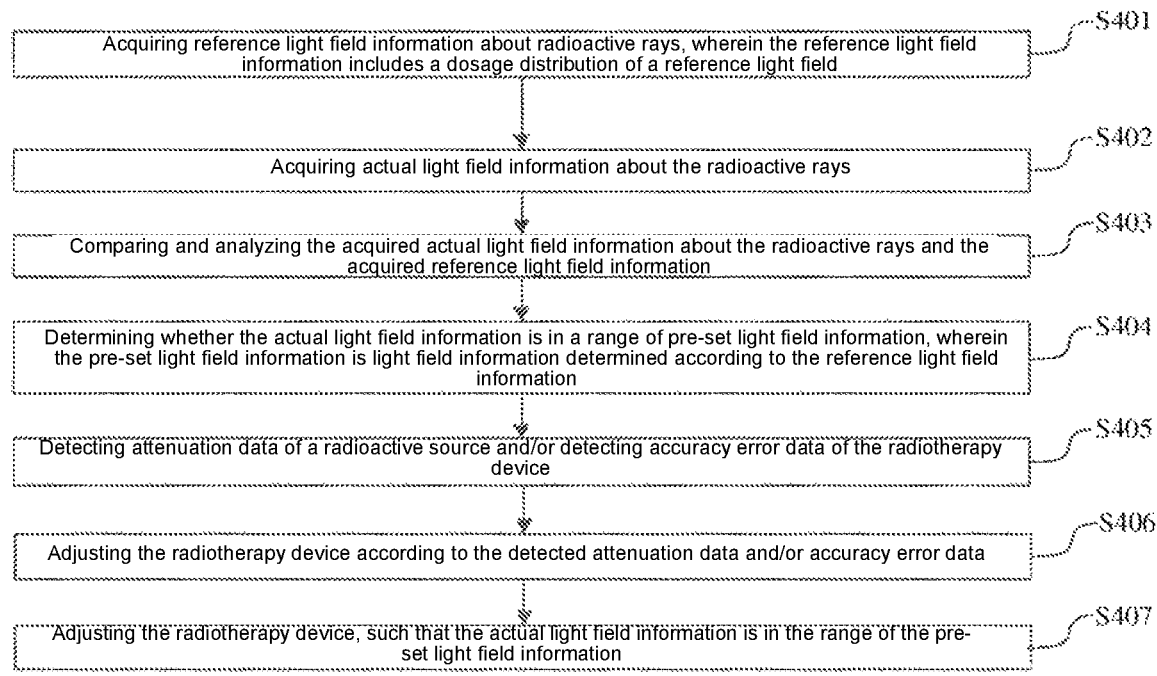
FIG. 6 is a schematic flow chart of a dosage verification method for a radiotherapy device according to yet still another embodiment of the present disclosure.

FIG. 6 is a schematic flow chart of a dosage verification method for a radiotherapy device according to yet still another embodiment of the present disclosure. As shown in FIG. 6, based on the above embodiment, the dosage verification method for a radiotherapy device includes:

Step S401: acquiring reference light field information about radioactive rays, wherein the reference light field information is initial light field information of the radiotherapy device and includes a dosage distribution of a reference light field;

Step S402: acquiring actual light field information about the radioactive rays, wherein the actual light field information is light field information generated according to received radioactive rays used for treatment during a radiotherapy process;

Step S403: comparing and analyzing the acquired actual light field information about the radioactive rays with the acquired reference light field information;

Step S404: determining whether the actual light field information is in a range of pre-set light field information, wherein the pre-set light field information is light field information determined according to the reference light field information;

Step S405: detecting attenuation data of a radioactive source and/or detecting accuracy error data of the radiotherapy device;

Step S406: adjusting the radiotherapy device according to the detected attenuation data and/or accuracy error data; and Step S407: adjusting the radiotherapy device, such that the actual light field information is in the range of the pre-set light field information.

In the present embodiment, when the difference data or the relevance data after the comparison and analysis in the step S403 exceeds the pre-set threshold, it is determined in the step S404 that the actual light field information is not in the range of the pre-set light field information, and it is verified that the radiation dosage of the current radiotherapy device does not meet the pre-set dosage requirements. At this time, the radiation dosage needs to be further adjusted to meet the expected dosage requirements. Specifically, in the present embodiment, when it is verified that the current radiation dosage does not meet the pre-set dosage requirements, the attenuation data of the radioactive source or the mechanical and electrical accuracy error data of the radiotherapy device can be detected, and radiation dosage compensations of the radioactive source can be carried out according to the attenuation data, or an accuracy calibration of the radiotherapy device can be carried out according to the mechanical and electrical accuracy error data. Thereby, accurate treatment is achieved and the radiotherapy accuracy and therapeutic effect are improved.

Exemplarily, the detected dosage of the radioactive rays in the actual light field information is smaller than the dosage of the radioactive rays in the reference light field information. By detecting the attenuation data of the radioactive source and/or the accuracy error data of the radiotherapy device, it can be determined whether this problem is caused by the attenuation of the radioactive source or the accuracy error of the radiotherapy device. If this problem is caused by the attenuation of a radioactive source, the radioactive source may be replaced to meet the expected dosage requirements. If this problem is caused by the accuracy error of the radiotherapy device, the radiotherapy device may be adjusted to reduce the error, or several compensations may be made to make the patient's treatment meet the expected dosage requirements.

Figure 7:
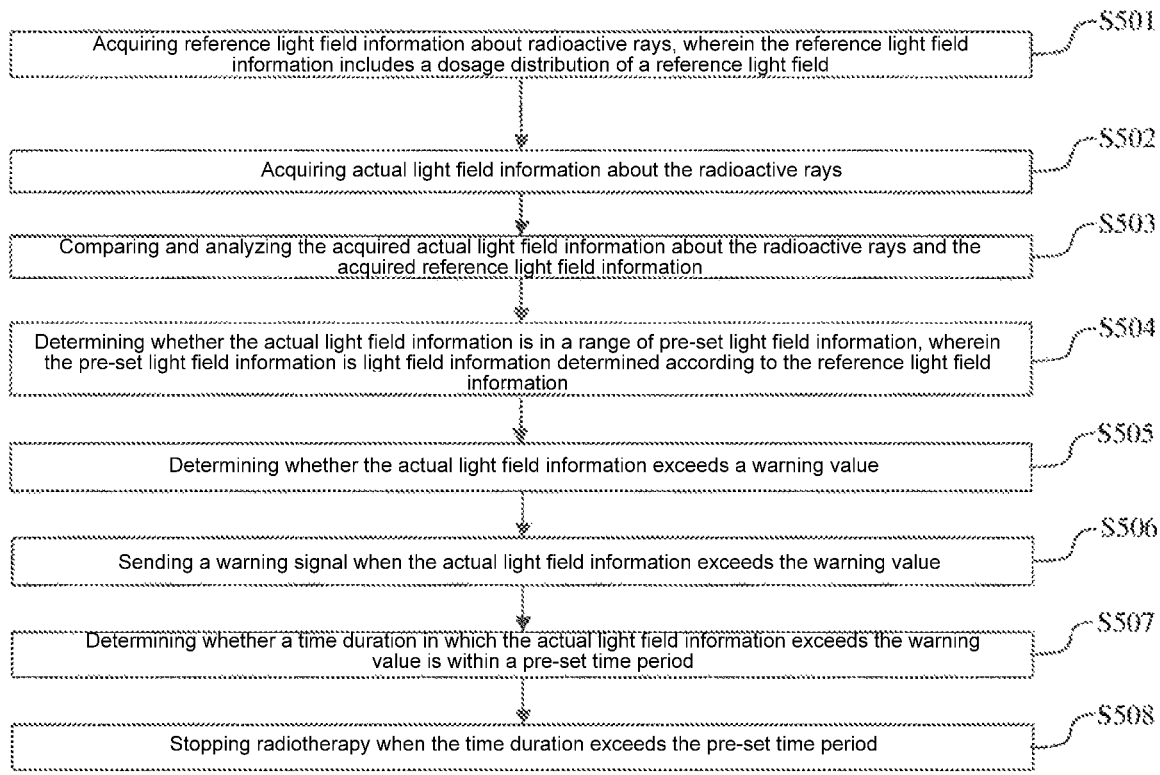
FIG. 7 is a schematic flow chart of a dosage verification method for a radiotherapy device according to yet still another embodiment of the present disclosure.

FIG. 7 is a schematic flow chart of a dosage verification method for a radiotherapy device according to yet still another embodiment of the present disclosure. As shown in FIG. 7, the dosage verification method for a radiotherapy device includes:

step S501: acquiring reference light field information about radioactive rays, wherein the reference light field information is initial light field information of the radiotherapy device and includes a dosage distribution of a reference light field;

Step S502: acquiring actual light field information about the radioactive rays, wherein the actual light field information is light field information generated according to received radioactive rays used for treatment during a radiotherapy process;

Step S503: comparing and analyzing the acquired actual light field information about the radioactive rays and the acquired reference light field information;

Step S504: determining whether the actual light field information is in a range of pre-set light field information, wherein the pre-set light field information is light field information determined according to the reference light field information;

Step S505: determining whether the actual light field information exceeds a warning value;

Step S506: sending a warning signal when the actual light field information exceeds the warning value;

Step S507: determining whether a time duration in which the actual light field information exceeds the warning value is within a pre-set time period; and Step S508: stopping radiotherapy when the time duration exceeds the pre-set time period.

In the present embodiment, a warning value of maximum allowable deviation of the light field information is preset. When the actual light field information deviates greatly beyond the warning value, a warning signal is sent out, e.g. a warning signal light flashes or a warning sound is sent out. The radiotherapy staff can take emergency measures in time, e.g. temporarily turn off the power supply or adjust the position of the radioactive light field according to the warning signal to avoid damage to the patient's body in time caused by excessive radiation dosages or deviation of the target of the radioactive light field, thereby improving the safety of the radiotherapy. Besides, it is detected in real time whether the time duration in which the actual light field information exceeds the warning value is within the pre-set time period. The radiotherapy is stopped when it is found that the time duration has exceeded the pre-set time period, so as to avoid serious damage to the patient's body due to long time radiation caused by excessive radiation dosages or deviation of the target of the radioactive light field, thereby improving the safety of the radiotherapy.

Figure 8:
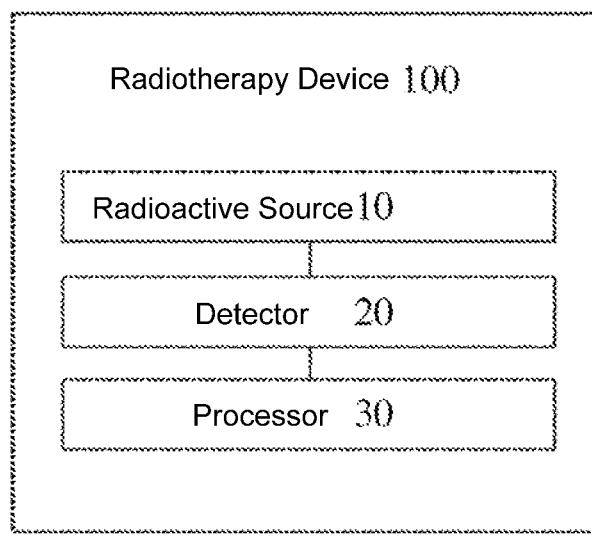
FIG. 8 is a schematic diagram showing a structure of a radiotherapy device according to an embodiment of the present disclosure.

FIG. 8 is a schematic diagram of a structure of a radiotherapy device 100 according to an embodiment of the present disclosure. Based on the above method embodiment, the radiotherapy device 100 includes a radioactive source 10, a detector 20 and a processor 30.

In the present embodiment, the radioactive source 10 may be a radioactive source of any type, e.g. a radioactive source of a cobalt 60 gamma ray for emitting gamma (γ) rays. The detector 20 is configured to receive the radioactive rays which are emitted by the radioactive source 10 and then pass through the matched collimator. The processor 30 is configured to acquire light field information about radioactive rays according to the radioactive rays received by the detector 20, compare and analyze acquired actual light field of radioactive rays and acquired reference light field, and determine whether the actual light field information is in a range of pre-set light field information.

The reference light field information refers to initial light field information configured in the radiotherapy plan when the radiotherapy device 100 leaves the factory. The reference light field information may include such information as a dosage distribution of the reference light field, a shape of the light field, a location of the light field, a dosage of the radioactive rays, and an intensity distribution of the radioactive rays in a range of the light field. In the present embodiment, when real-time dosage verification is performed, reference light field information of radioactive rays such as dosage distributions of the reference light field at various time points and treatment locations can be acquired from the radiotherapy planning system. In other embodiments, when non-real-time dosage verification is performed, pre-measured reference light field information of the radioactive rays such as the dosage distribution of the reference light field can also be obtained by confirming an opening degree of a collimator with a size to be measured according to actual needs and treatment experience.

In the present embodiment, when real-time dosage verification is performed, the detector 20 can acquire the actual light field information about the radioactive rays sequentially, such as a dosage distribution of the actual light field, a shape of the light field, a location of the light field, a dosage of radioactive rays, and an intensity distribution of the radioactive rays in a range of the light field during the radiotherapy process. The actual light field information is light field information generated according to the radioactive rays received by the detector 20 during the radiotherapy process. In other embodiments, when non-real-time dosage verification is performed, the detector 20 can acquire the actual light field information of the radioactive rays, such as the dosage distribution of the actual light field by opening the collimator according to the correspondingly preset opening degree.

In the present embodiment, the processor 30 compares and analyzes the actual light field information about the radioactive rays acquired by the detector 20 and the acquired reference light field information, to obtain difference data between them through analysis, or obtain relevance data between them through similarity index analysis. In the present embodiment, when the difference data or the relevance data after comparison and analysis does not exceed a preset threshold, the processor 30 determines that the actual light field information is in the range of the pre-set light field information, and verifies that the radiation dosage of the current radiotherapy device meets the expected dosage requirements, and thus it is unnecessary to further adjust the radiation dosage. When the difference data or the relevance data after comparison and analysis exceeds the pre-set threshold, the processor 30 determines that the actual light field information is not in the range of the pre-set light field information, and verifies that the radiation dosage of the current radiotherapy device does not meet the pre-set dosage requirements, and thus the radiation dosage may be further adjusted to meet the expected dosage requirements.

In the radiotherapy device 100 of the present embodiment, the detector 20 acquires the reference light field information and the actual light field information of the radioactive rays of the radioactive source 10, and the processor 30 determines whether the actual light field information is in a range of the pre-set light field information, to verify whether the radiation dosage of the current radiotherapy device conforms to the requirement of the expected dosage. This enables convenient, fast and accurate verification of the dosage of the radiotherapy device, and improves the efficiency and accuracy of verification of the radiation dosage. Furthermore, it does not need to measure the radiation dosage manually, and improves the safety of radiation dosage verification. Besides, dosage verification may be performed in real time during the radiotherapy process.

In another embodiment of the present disclosure, the processor 30 is further configured to store the actual light field information, and determine a treatment plan according to the actual light field information. When the difference data or the relevance data after comparison and analysis by the processor 30 exceeds the pre-set threshold, the processor 30 determines that the actual light field information is not in the range of the pre-set light field information, and verifies that the radiation dosage of the current radiotherapy device does not meet the pre-set dosage requirements. At this time, the radiation dosage needs to be further adjusted to meet the expected dosage requirements. Specifically, the processor 30 stores the actual light field information, and adjusts the current treatment plan or the next treatment plan according to the actual light field information, so that the radiation dosage at the time of the current treatment or the next treatment meets the expected dosage requirements. This achieves precise treatment and improves the radiotherapy accuracy and therapeutic effect.

In still another embodiment of the present disclosure, the processor 30 is further configured to adjust the radiotherapy device according the actual light field information, such that the actual light field information meets the light field requirements in the radiotherapy planning system. When the difference data or the relevance data after comparison and analysis by the processor 30 exceeds the pre-set threshold, the processor 30 determines that the actual light field information is not in the range of the pre-set light field information, and verifies that the radiation dosage of the current radiotherapy device does not meet the pre-set dosage requirements. At this time, the radiation dosage needs to be further adjusted to meet the expected dosage requirements. Specifically, the processor 30 controls the movement of the treatment couch or the treatment head via a control system of the radiotherapy device to adjust a radial distance between the treatment head and the therapeutic target, so that the actual light field information falls within the range of the pre-set light field information, so as to adjust the radiation dosage to meet the expected dosage requirements, thereby achieving precise treatment, and improving the radiotherapy accuracy and therapeutic effect. In other embodiments, the processor 30 can also adjust hardware devices such as the treatment head or radioactive source, such that the actual light field information falls within the range of the pre-set light field information.

In yet still another embodiment of the present disclosure, the processor 30 is further configured to determine a time duration in which the actual light field information is in the range of the pre-set light field information or in which the actual light field information exceeds the range of the pre-set light field information; and configured to determine whether the time duration is within a pre-set time period, and stop radiotherapy when the time duration exceeds the pre-set time period. In the present embodiment, a warning value of maximum allowable deviation of the light field information is preset by a setting module. When the actual light field information deviates greatly beyond the warning value, a warning signal is sent out, e.g. a warning signal light flashes or a warning sound is sent out. The radiotherapy staff can take emergency measures in time, e.g. temporarily turn off the power supply or adjust the position of the radioactive light field according to the warning signal to avoid damage to the patient's body in time caused by excessive radiation dosages or deviation of the target of the radioactive light field, thereby improving the safety of the radiotherapy. Besides, the processor 30 detects in real time whether the time duration in which the actual light field information exceeds the warning value is within the pre-set time period, and stops the radiotherapy when it confirms that the time duration has exceeded the pre-set time period, so as to avoid serious damage to the patient's body due to long time radiation caused by excessive radiation dosages or deviation of the target of the radioactive light field, thereby improving the safety of the radiotherapy.

In yet still another embodiment of the present disclosure, the processor being further used for storing the actual light field information and determining the treatment plan according to the actual light field information, specifically includes: the processor being used for storing the actual light field information, and adjusting a current treatment plan according to the actual light field information; or for storing the actual light field information, and adjusting a next treatment plan according to the actual light field information.

In yet still another embodiment of the present disclosure, the processor is further used for acquiring attenuation data of the radioactive source and/or detecting accuracy error data of the radiotherapy device; and for adjusting the radiotherapy device according to the attenuation data and/or accuracy error data detected.

In yet still another embodiment of the present disclosure, the processor is further used for determining whether the actual light field information exceeds a warning value; and for sending a warning signal or stopping radiotherapy when the actual light field information exceeds the warning value.

In yet still another embodiment of the present disclosure, the light field information further includes at least one of a light field shape, a light field position, a dosage of the radioactive rays, and an intensity distribution in a light field range. In some examples, the light field information includes a light field shape, and a dosage of the radioactive rays. In some other examples, the light field information includes a light field shape, a light field position, and an intensity distribution in a light field range.

It will be understood that various parts of the present disclosure may be implemented by hardware, software, firmware or combinations thereof. In the above embodiments, a plurality of steps or methods may be implemented by software or firmware stored in a memory and executed by an appropriate instruction execution system. For example, if the plurality of steps or methods are implemented by hardware, as in another embodiment, they can be implemented by any of the following techniques known in the art or the combinations thereof: discrete logic circuits with logic gates for realizing logical functions for data signals, special integrated circuits with suitable combinational logic gates, programmable gate arrays (PGA), field programmable gate arrays (FPGA), etc.

In the description of this specification, reference terms "one embodiment", "some embodiments", "examples", "specific examples", or "some examples" mean that specific features, structures, materials or features described in conjunction with the embodiment or example are included in at least one embodiment or example of the present disclosure. In this specification, the exemplary expression of the above terms does not necessarily refer to a same embodiment or example. Furthermore, the described specific features, structures, materials or characteristics can be combined in a suitable manner in any one or more embodiments or samples.

Although embodiments of the present disclosure have been shown and described, a person of ordinary skill in the art can understand that various changes, modifications, substitutions and variations can be made to these embodiments without departing from the principles and purposes of the present disclosure, and the scope of the present disclosure is defined by the claims and their equivalents.

What is claimed is:

1. A dosage verification method for a radiotherapy device, applied to the radiotherapy device, the dosage verification method comprising:
   acquiring reference light field information about radioactive rays, wherein the reference light field information is initial light field information of the radiotherapy device, and comprises a dosage distribution of a reference light field;
   acquiring actual light field information about the radioactive rays, wherein the actual light field information is light field information generated according to received radioactive rays used for treatment during a radiotherapy process;
   comparing and analyzing the actual light field information about the radioactive rays and the reference light field information;
   determining whether the actual light field information is in a range of pre-set light field information, wherein the pre-set light field information is light field information determined according to the reference light field information; and
   adjusting a radial distance between a treatment head and a therapeutic target such that the actual light field information is in the range of the pre-set light field information, wherein
   before adjusting the radial distance between the treatment head and the therapeutic target, the method further comprises;
   detecting attenuation data of a radioactive source and detecting accuracy error data of the radiotherapy device; and
   adjusting the radiotherapy device according to the attenuation data and the accuracy error data detected.

2. The dosage verification method for the radiotherapy device according to claim 1, wherein during the radiotherapy process, the method further comprises:
   determining whether the actual light field information exceeds a warning value; and
   sending a warning signal when the actual light field information exceeds the warning value.

3. The dosage verification method for the radiotherapy device according to claim 2, the dosage verification method further comprising:
   determining whether a time duration in which the actual light field information exceeds the warning value is within a pre-set time period, and
   stopping radiotherapy when the time duration exceeds the pre-set time period.

4. The dosage verification method for the radiotherapy device according to claim 1, wherein the light field information further comprises at least one of a light field shape, a light field position, a dosage of the radioactive rays, and an intensity distribution in a light field range.

5. A radiotherapy device, comprising:
   a radioactive source for emitting radioactive rays;
   a detector for receiving the radioactive rays emitted by the radioactive source; and
   a processor for acquiring actual light field information about the radioactive rays according to the radioactive rays received by the detector, comparing and analyzing the actual light field information of the radioactive rays and the reference light field information acquired, determining whether the actual light field information is in a range of pre-set light field information, adjusting a radial distance between a treatment head and a therapeutic target according to the actual light field information such that the actual light field information meets light field requirements in a radiotherapy planning system, acquiring attenuation data of the radioactive source and detecting accuracy error data of a radiotherapy device, and adjusting the radiotherapy device according to the attenuation data and the accuracy error data detected, wherein before adjusting the radial distance between the treatment head and the therapeutic target, the processor detects the attenuation data of the radioactive source and the accuracy error data of the radiotherapy device, and adjusts the radiotherapy device according to the attenuation data and the accuracy error data detected,
   wherein the reference light field information is initial light field information of the radiotherapy device, the actual light field information is light field information generated according to the radioactive rays received by the detector during a radiotherapy process, and the pre-set light field information is light field information determined according to the reference light field information.

6. The radiotherapy device according to claim 5, wherein the processor is further used for determining a time duration in which the actual light field information is within the range of the pre-set light field information or in which the actual light field information exceeds the range of the pre-set light field information; and for determining whether the time duration is within a pre-set time period, and for stopping radiotherapy when the time duration exceeds the pre-set time period.

7. The radiotherapy device according to claim 5, wherein the processor is further used for determining whether the actual light field information exceeds a warning value; and for sending a warning signal or stopping radiotherapy when the actual light field information exceeds the warning value.

8. The radiotherapy device according to claim 5, wherein the light field information further comprises at least one of a light field shape, a light field position, a dosage of the radioactive rays, and an intensity distribution in a light field range.

* * * * *